United States Patent [19]
Sadlo

[11] Patent Number: 6,095,145
[45] Date of Patent: Aug. 1, 2000

[54] PROPHYLACTIC

[76] Inventor: Frank C. Sadlo, P.O. Box 32222, Louisville, Ky. 40232

[21] Appl. No.: 09/228,728

[22] Filed: Jan. 12, 1999

[51] Int. Cl.[7] .......................................................... A61F 6/04
[52] U.S. Cl. ............................................ 128/844; 128/918
[58] Field of Search ..................................... 128/842, 844, 128/918; 604/347, 353

[56] References Cited

U.S. PATENT DOCUMENTS

| | | | |
|---|---|---|---|
| 4,846,197 | 7/1989 | Benjamin | 604/353 |
| 4,942,885 | 7/1990 | Davis | 128/842 |
| 5,163,449 | 11/1992 | van der Valk | 128/844 |
| 5,531,230 | 7/1996 | Bell | 128/844 |

*Primary Examiner*—Michael A. Brown
*Attorney, Agent, or Firm*—Tod R. Nissle, P.C.

[57] ABSTRACT

A package for a condom permits lubricant to be stored in the package such that only the inside or outside of the condom contacts the lubricant. A three-dimensional computer file of an individual's erect penis is utilized to provide a custom fitting condom for the individual's penis.

2 Claims, 3 Drawing Sheets

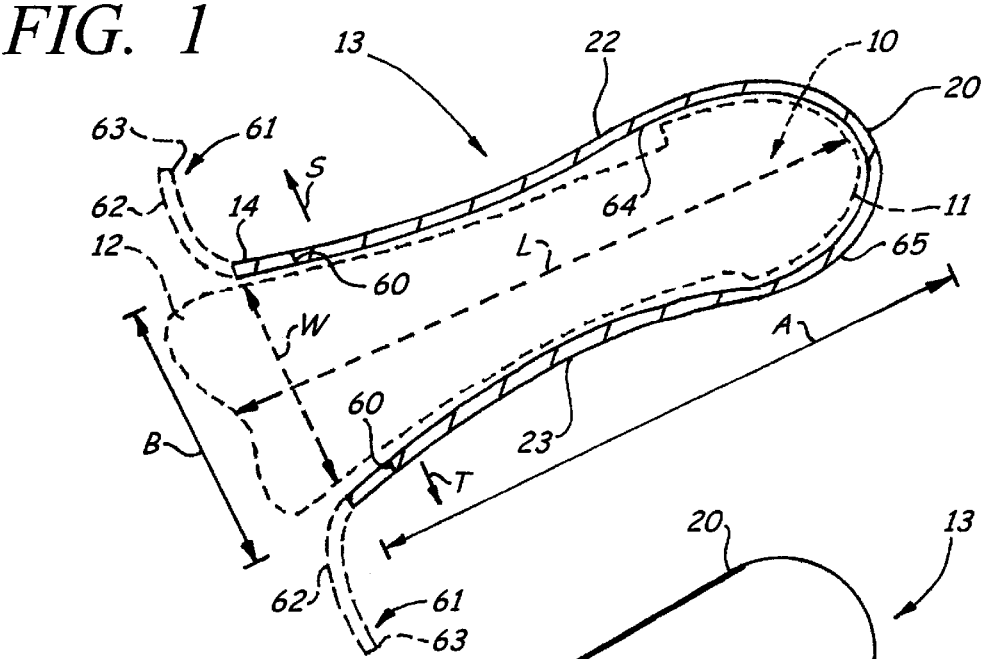
FIG. 1
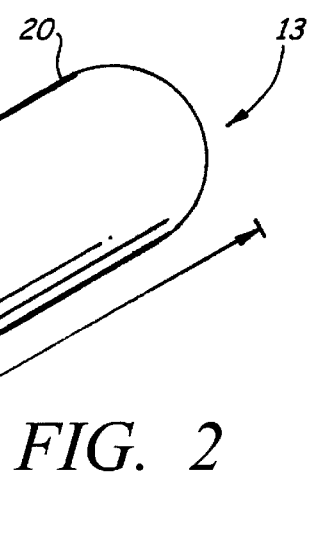
FIG. 2
FIG. 3
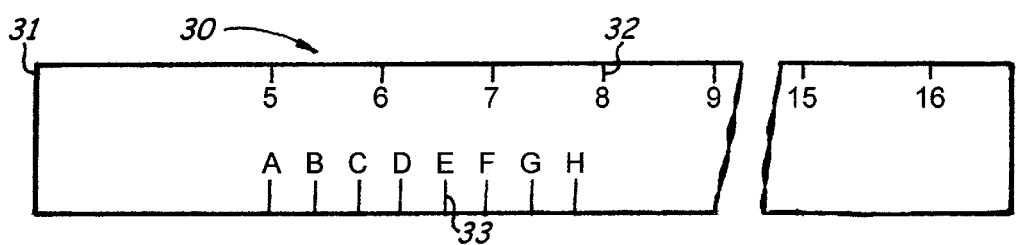

```
┌─────────────────────────────────┐
│ PRODUCE COMPUTER BASED FILE     │
│ REPRESENTING THREE-             │
│ DIMENSIONAL SCAN OF             │
│ SELECTED ERECT PENIS    50      │
└─────────────────────────────────┘
              │
              ▼
┌─────────────────────────────────┐
│ USE COMPUTER BASED FILE TO      │
│ PRODUCE THREE DIMENSIONAL       │
│ MODEL OF ERECT PENIS    51      │
└─────────────────────────────────┘
              │
              ▼
┌─────────────────────────────────┐
│ DIP THREE DIMENSIONAL           │
│ MODEL OF ERECT PENIS IN         │
│ LATEX TO PRODUCE                │
│ ANATOMICALLY CORRECT            │
│ CONDOM                  52      │
└─────────────────────────────────┘
```

*FIG. 6*

PROPHYLACTIC

This invention relates to a prophylactic.

More particularly, the invention relates to a prophylactic apparatus which reduces the risk that a venereal disease will be treated during sexual intercourse and reduces the risk that the prophylactic will, in use, cause physical injury.

Prophylactics, or condoms, have long been utilized during sexual intercourse to prevent the transmission of venereal disease. Such prophylactics are typically fabricated from latex and have a generally cylindrical shape with a closed end and an open end. Prior to packaging, each prophylactic is rolled from the open end toward the closed end in a well known conventional fashion. In use, the prophylactic is installed by placing the rolled prophylactic on the distal end of an erect penis and unrolling the prophylactic down over the length of the penis. In many cases, the prophylactic can not be completely unrolled, and a rolled portion remains at the base of the penis. Although prophylactics have been useful in reducing the incidence of venereal disease, several disadvantages have long been associated with their use. First, prophylactics are marketed in two sizes a "regular" size and a "large" size. Regular prophylactics are believed to be too large for about 15% of the male population. Large prophylactics are too small for others in the male population. The inability of some men to use a prophylactic increases the incidence of AIDS and other venereal diseases. Second, the rolled portion which remains after a prophylactic is installed tends to roll back up the penis and, even when the rolled portion stays in position, produces a tourniquet effect which pinches and can potentially damage nerve ending by restricting blood circulation. One reason that the rolled portion of an installed prophylactic tends to roll back up the penis is that the base of the penis flares.

Accordingly, it would be highly desirable to provide an improve prophylactic which would decrease the incidence of venereal disease and would reduce the risk of physical injury during use of the prophylactic.

Therefore, it is a principal object of the invention to provide an improved prophylactic.

A further object of the invention is to provide an improved prophylactic which minimizes the likelihood that nerve endings in the base of a penis will be injured during use of the prophylactic.

Another object of the invention is to provide an improved prophylactic which reduces the risk that the prophylactic will move off the penis during use.

Still a further object of the invention is to provide an improved prophylactic which can be utilized by each adult male in the population.

Yet another object of the invention is to provide prophylactic apparatus which enables a male to determine the shape and dimension of prophylactic which reduces the risk of injury and of transmission of venereal disease.

These and other, further and more specific, objects and advantages of the invention will be apparent to those skilled in the art from the following detailed description thereof, taken in conjunction with the drawings, in which:

FIG. 1 is a side section view illustrating an elastic latex prophylactic constructed and used in accordance with the principles of the invention;

FIG. 2 is a side view further illustrating the prophylactic of FIG. 1;

FIG. 3 is a top view of a pliable measuring tape utilized to determine the size of prophylactic utilized on an erect penis having a particular length and width;

Figure 4:
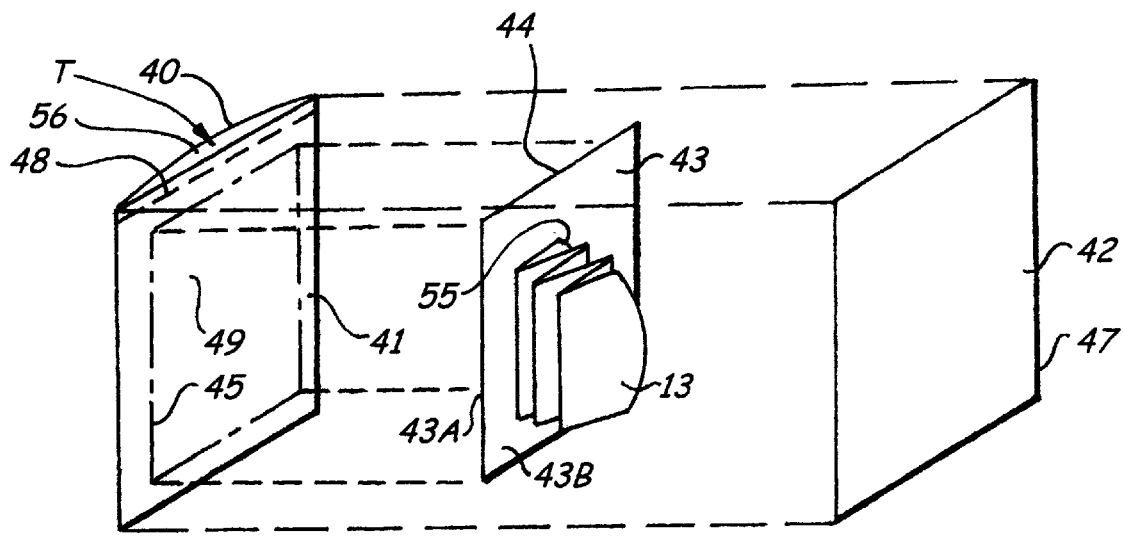
FIG. 4 is a perspective view illustrating a packaging apparatus used in accordance with the invention.

Briefly, in accordance with my invention, I provide an article of manufacture comprising a package including a first layer of material; a second layer of material sealed to the first layer; a condom mounted on the second layer of material; and, a third layer of material attached to said the layer to enclose the second layer and the condom intermediate the first and second layers.

In another embodiment of the invention, I provide an article of manufacture comprising a package including a first layer of material; a second layer of material sealed to the first layer; a condom mounted on the second layer of material; a third layer of material attached to the first layer to enclose the second layer and the condom intermediate the first and second layers; and, lubricant sealed between one of a pair including the first layer and the second layer, and the second layer and the third layer.

In a further embodiment of the invention, I provide a method of producing a condom, including the steps of producing a computer file defining in three dimensions a selected erect penis; utilizing the computer file to produce a model of the selected erect penis; and, utilizing the model to produce a condom.

In still another embodiment of the invention, I provide a method of fitting an individual with a condom, including the steps of producing reference data defining in three dimensions the shape and dimension of a plurality of erect reference penises each having a different shape and dimension; producing control data defining in three dimensions the shape of a particular individual's erect penis; comparing the control data to the reference data to select one of the reference penises as closest in shape and dimension to the individual's erect penis; and, utilizing the one of the reference penises selected to provide a condom for the particular individual's erect penis.

In still a further embodiment of the invention, I provide an article of manufacture comprising a package including a first layer of material; a second layer of material sealed to said first layer; and, a condom sealingly mounted on one of said layers intermediate said layers. The article of manufacture can include at least one indicia indicating the preferred orientation of the condom on a user's erect penis.

Turning now to the drawings, which depict the presently preferred embodiments of the invention for the purpose of illustrating the practice thereof and not by way of limitation of the scope of the invention, and in which like references characters refer to corresponding elements throughout the several views, FIG. 1 illustrates an elastic latex prophylactic, or condom, 13 installed on an erect penis 10. The prophylactic 13 includes a closed end 20 which fits over the distal end or head 11 of the penis 10. The prophylactic also includes an open end 14 which fits over the base 14 of penis 10. The length of erect penis 10 is indicated by arrows L. The greatest width of penis 10 is indicated by arrows W. When prophylactic 13 is installed on penis 10, the length of prophylactic 13 is indicated by arrows A and the width of prophylactic 13 is indicated by arrows B.

As shown in FIG. 2, when prophylactic 13 is in its normal configuration and has not been installed on and conformed to the shape and dimension of penis 10, prophylactic 13 has a generally cylindrical hollow configuration. The open end 14 of prophylactic 13 can, if desired, have the flared shaped indicated by dashed lines 19 so that end 14 better conforms to the flared base 12 of penis 10. In FIG. 2, the length of prophylactic 13 is indicated by arrows D and the width by arrows C. The length D is generally equivalent to the length A after the prophylactic has been installed on an erect penis 10. The width C is generally less than the width B because prophylactic 13 preferably elastically expands to fit over erect penis 10. The elastic expansion of prophylactic 13 helps to produce a seal between penis 10 and the cylindrical portion of prophylactic 13 which extends over the sides and base of penis 10.

If desired, the open end 14 of prophylactic 13 can consist of latex having a thickness greater than that of the closed end 20 and sides of the prophylactic 13 extending between end 20 and end 14. End 14 can also, if desired, be ribbed. The inner surface of end 14 can, if desired, be coated with contact adhesive or other adhesive. One potential function of utilizing thicker latex, ribs, or adhesive on or in end 14 is to make end 14 more resistant to rolling up penis 10 away from base 12 toward head 11.

It is preferred that the length A of prophylactic 13 be equal to or somewhat less (typically preferably about 1% to 20% less) than the length L of penis 10. It is also preferred, but not required, that prophylactic 13 not be rolled in conventional fashion, but instead simply be folded and placed in a conventional square foil packet or other package. When utilized in conjunction with the fitting procedure described below, a prophylactic 13 which has not been rolled during packaging is believed to provide significantly more comfort and significantly less risk of rolling up than a conventional prophylactic.

In one preferred embodiment of the invention, prophylactics are pro vided in a variety of lengths. Each length is provided in a variety of widths or circumferences. Indicia identify the size, i.e., the length and circumference, of each condom. While the indicia can be imprinted or otherwise formed on the condom, they more commonly are printed on the package in which the condom is stored. Although any desired indicia can be utilized, one proposed system is shown below in Tables I and II.

TABLE I

Condom Length Indicia

| Length Indicia | Actual Length of Condom (mm) | Preferred Length of Penis (mm) |
|---|---|---|
| 5 | 90 | 80 to 90 |
| 6 | 115 | 91 to 115 |
| 7 | 140 | 116 to 140 |
| 8 | 165 | 141 to 165 |
| 9 | 190 | 166 to 190 |
| 10 | 215 | 191 to 215 |
| 11 | 240 | 216 to 240 |
| 12 | 265 | 241 to 265 |
| 13 | 290 | 266 to 290 |
| 14 | 315 | 291 to 315 |
| 15 | 340 | 316 to 340 |
| 16 | 365 | 341 to 365 |

TABLE II

Condom Width/Circumference Indicia*

| Width Indicia | Actual Circumference of Condom | Maximum Circumference of Erect Penis (mm) |
|---|---|---|
| A | 80 | 90 |
| B | 90 | 100 |
| C | 100 | 110 |
| D | 110 | 120 |
| E | 120 | 130 |
| F | 130 | 140 |
| G | 140 | 150 |
| H | 150 | 160 |

*Each length condom preferably is provided in each of the widths indicated in Table II. Consequently, a condom with a length of 11 is provided in each of the widths A to H so that there is a size 11A condom, size 11B condom, size 11C condom, size 11D condom, etc.

By way of example, with reference to Tables I and II, when the indicia 11E appear on a package containing a condom or appear on a condom, then the condom has a length of 240 mm and a circumference of 120 mm. When the indicia 5G appear on a package containing a condom, then the condom has a length of 90 mm and a circumference of 140 mm. When the indicia 5B appear on a package containing a condom, the condom has a length of 90 mm and a circumference of 90 mm.

As noted in Table I, the length of a condom utilized in accordance with the invention preferably is equal to or less than the length of an erect penis to reduce the risk that the condom will tend to roll up and off the penis.

As noted in Table II, the actual width (or circumference) of a condom is preferably less than the width (or circumference) of an erect penis because the stretching of the condom to conform to an erect penis is important in creating a seal between the condom and penis and in maintaining the condom on the penis.

FIG. 3 illustrates a tool comprising pliable strip 30 of fabric, plastic, or other material which can be utilized to measure the size of an erect penis, to correlate the size with the condoms provided in accordance with Tables I and II above, and to enable the user to select an appropriate size condom. As would be appreciated by those of skill in the art, two separate strips can be utilized, each bearing one of the pair of scales on strip 30. In use of the strip 30, end 31 is placed at the base of the user's erect penis and strip 30 is extended from the penis base to the tip of the penis. If, for example, the tip of the penis is at rule mark 32, then the length of the appropriate condom to be utilized by the user is indicated by indicia "8". The user then circumferentially wraps strip 30 around the portion of his erect penis having the greatest circumference. If, for example, the circumference of the user's erect penis is indicated by the distance from end 31 to rule mark 33, then the width of the appropriate condom to be utilized by the user is indicated by the indicia "E". The distance from end 31 to the rule mark 33 is 130 mm. The circumference of a condom with an "E" width indicia is only 120 mm. After measuring the length and circumference of his erect penis in the manner just described, the user selects a size 8E condom and draw it over his erect penis 10 to the position shown in FIG. 1. Since the circumference of the 8E condom is less than the circumference of the user's erect penis 10, the condom elastically stretches when pulled over penis 10. An alternate method a user can employ to select an appropriate condom size is to simply try on different ones of the condoms listed in Tables I and II until the appropriate size is identified.

One advantage of providing a condom with a flared open end 19 is that the flared end tends to stretch radially outwardly in the directions indicated by arrows S and T an amount which is about equal to the amounts that the side portions 22 and 23 of the condom stretch radially outwardly when the condom is installed on an erect penis 10. Such uniform stretching tends to avoid the tourniquet effect produced at the base 12 by the rolled portion of a conventional condom. Simply the fact that condoms utilized in accordance with the presently preferred embodiment of the invention do not include a rolled portion also tends to eliminate the tourniquet effect produced by conventional condoms and to uniformly distribute along most of the length of erect penis 10 the compressive forces generated against penis 10 by elastically stretched condom 13.

Another embodiment of the invention is illustrated in FIG. 4. A condom 13 is mounted on a rectangular panel or card 43. In FIG. 4, condom 13 is folded. If desired, condom 13 can be rolled in conventional fashion. A circular, oval, or other shaped opening 55 is formed through card 43. The bottom open end of condom 13 is mounted on card 43 such that it circumscribes opening 55 and opens onto the back side 43A of card 43. The majority of condom 13 is on the front side 43B of card 43. Card 43 includes outer rectangular peripheral edge 44. Card 43 is sealed inside a package including a first layer 42 of material having an outer rectangular peripheral edge 47. Layer 42 is typically fabricated from a foil material, but can comprise any desired material. Second 40 and third 41 rectangular layers of material of equal shape and dimension are sealed together in registration along three of four sides to form a pocket having an opening or mouth 56 through which condom 13 can be inserted in the direction of arrow T in FIG. 4. The rectangular outer edge 44 is smaller than and fits within the rectangular outer edges of each of layers 40, 41, and 42. The periphery of back side 43A near edge 44 is removably sealed to layer 41 along rectangular dashed line 45. Sealing edge 44 without sealing the remainder of back side 43A permits lubricant to be inserted intermediate back side 43A and the area 49 of layer 41 circumscribed by line 45. Since lubricant intermediate side 43A and area 49 can not escape outwardly intermediate edge 44 and layer 41, the lubricant only reaches the inside of condom 46 and cannot reach the outside of condom located on side 43B of layer 43. Alternatively, after edge 44 is removably sealed to layer 41, lubricant can be applied to front side 43B and the outer portion of condom 46 before the peripheral edge 47 of layer 42 is sealed to the peripheral edge of layer 41. In this embodiment, the lubricant on side 43B is unable to penetrate intermediate edge 44 and layer 41 into area 49 of layer 41. Opening 55 is shaped and dimensioned to prevent lubricant in area 49 from penetrating through opening onto the outer surface of condom 13; and, when lubricant is applied on side 43B, to prevent lubricant to penetrate through opening 55 into area 49 and the inside of condom 13. If desired, the bottom or another portion of condom 13 can removably sealingly engage a portion of side 43A or side 43B to prevent lubricant from passing through opening 55. If desired, lubricant need not be utilized on either side 43A or 43B of layer 43, or, can be utilized on each side 43A, 43B.

In another embodiment of the invention similar to that illustrated in FIG. 4, layer 41 is eliminated (but all the other layers illustrated in FIG. 4 remain) such that layer 40 functions like layer 41, i.e., the peripheral edge 44 of layer 43 is removably sealed to layer 40 and lubricant can be included on side 43A intermediate layer 40 and side 43A or can be include on side 43B intermediate side 43B and layer 42. The peripheral edge 47 of layer 42 is in registration with and is sealed to the peripheral edge of layer 40 to form a mouth 56 (in the same manner that layers 40, 41 form mouth 56). Means are provided to sealingly open and close the mouth 56.

In use of the embodiment of the invention illustrated in FIG. 4, layer 42 is peeled off of layer 41 to expose condom 13 and layer 43. Condom 13 is removed from layer 43 and is unfolded and slid onto an erect penis; or, in the alternative, layer 43 is peeled off and removed from layer 41. Layer 43 is utilized as a grip to facilitate pulling condom 13 onto an erect penis by unfolding condom 13, by grasping layer 43 and pulling opening 55 over an erect penis such that the penis slides through opening 55 into condom 13. After condom 13 is slid onto the erect penis, layer 43 is removed from condom 13 or is left on condom 13. Condom 13 can be removably attached to layer 43 by adhering end 14 to card 43 with adhesive which permits end 14 to be peeled off card 43.

A used condom 13 is slipped in the direction of arrow T through elongate mouth 56 into the pocket intermediate layers 40 and 41. Mouth 56 is sealed along a line indicated by dashed line 48. Mouth 56 can be sealed using a "ZIP LOCK" type seal found on plastic bags, using contact adhesive, or using any other desired fastening means. The fastening means is preferably already in the invention of FIG. 4 when a user purchases the invention.

In another embodiment of the invention, condom 13 includes a circular flange 61. An arcuate line of weakening 60 is formed (FIG. 1) to circumscribe the end 14 of the condom. The line of weakening 60 can be formed by perforating the condom 13, by applying heat or chemical means around end 14 to weaken and/or embrittle the material comprising condom 13, by partially die-cutting through end 14, or by any other desired means. This "flanged condom" can be used as follows.

First, the inner circumferential surface 62 can be removably adhered to the front side 43A of card 43 in FIG. 4 around opening 55 in order to seal closed the inside surface 64 of condom 13. Flange 61 circumscribes opening 55. Card 43 is removably sealed to layer 41 over area 49, and the rectangular outer edge 47 of layer 42 is placed in registration with and removably sealed to the rectangular outer edge of layer 41 in the manner earlier described. Layer 40 is sealed to layer 41 to produce a pocket with mouth 56. Condom 13 is sealed between layers 41 and 42. When the package of FIG. 4 is utilized, layer 42 is peeled off layer 41; card 43 is peeled off layer 41; card 43 is manually grasped and used to pull and slide condom 13 on an erect penis; card 43 is removed from condom 13 (typically by cutting or tearing the card); and, flange 61 is removed from condom 13 by separating flange 61 from condom 13 along line of weakening 60.

Second, in FIG. 4 the card 43 is eliminated and the inner circumferential surface 62 is removably adhered to a portion of area 49 on layer 41 in order to seal closed the inside surface 64 of a condom 13. The rectangular outer edge 47 of layer 42 is placed in registration with and removably sealed to the rectangular outer edge of layer 41 in the manner earlier described to enclose condom 13 intermediate layers 41 and 42. A lubricant can be included between layers 41 and 42 and will only contact the outer surface 65 (and not the inner surface 64) of condom 13 because sealing surface 62 to area 49 prevents the lubricant from reaching surface 64. Similarly, lubricant which is inside condom 13 and is contacting inner surface 64 cannot contact outer surface 65 because sealing surface 62 of area 49 prevents the lubricant from reaching outer surface 65. Layer 40 is sealed to layer 41 to produce a pocket with mouth 56. The resulting packet is utilized by peeling layer 42 off layer 41; removing flange 61 from layer 41; using flange 61 to pull and slide condom 13 onto an erect penis; and, separating flange 61 from condom 13 along line of weakening 60.

Third, the flanged condom 13 is utilized by pursing the halves of flange 61 and pressing the halves together (in much the same manner that the lips of a person's mouth are pursed together to seal closed the mouth) and by sealing together the resulting opposing portions of inner surface 62 which contact when the halves of flange 61 are pursed and pressed together. These opposing portions of surface 62 are sealed together with an adhesive which holds such opposing portions together and which later permits the opposing portions of surface 62 to be peeled apart. When the opposing portions of surface 62 are sealed together, then the inner surface 64 of condom 13 is sealed shut and lubricant contacting the outer surface 65 cannot contact surface 64, and vice-versa. In this embodiment of the invention, in FIG. 4 card 43 and layer 42 are dispensed with and are not utilized. The flanged condom with pursed, sealed flange 61 is placed in the resealable packet which includes layers 40 and 41 and includes means for opening and resealing the packet along line 48. When the flanged condom 13 is placed in the resealable packet, lubricant can (1) be only inside condom 13 contacting surface 64, (2) only be outside condom contacting surface 65, (3) be completely omitted and not included in the packet with condom 13 (in which case it is not necessary to seal together opposing pursed portions of surface 62), and (4) contact both surfaces 64 and 65 (in which case it is not necessary to seal together opposing pursed portions of surface 62). The resulting packet is utilized by opening the packet along line 48, by removing the flanged condom 13, by opening the mouth at end 14 of condom 13 by peeling apart the opposing adhering pursed portions of surface 62, by grasping flange 61 and utilizing flange 61 to pull condom 13 onto an erect penis, and, by tearing off flange 61 from condom 13 along line of weakening 60. After use, condom 13 is placed through mouth 56 back into the packet, and the packet is sealed along line 48.

Fourth, the flanged condom can be utilized by removably sealing circular surface 62 of flange 61 to a surface on the inside of packet in FIG. 4, which packet includes layers 40 and 41 and the means for fastening mouth 56 along line 48. The inner circumferential surface 62 is removably adhered inside the packet to layer 40 (or layer 41) in order to seal closed the inside surface 64 of a condom 13. A lubricant can be inserted inside the packet between layers 40 and 41 and will only contact the outer surface 65 (and not the inner surface 64) of condom 13 because sealing surface 62 to layer 40 prevents the lubricant from reaching surface 64. Similarly, lubricant which is inside condom 13 and is contacting inner surface 64 cannot contact outer surface 65 because sealing surface 62 to layer 40 prevents the lubricant from reaching outer surface 65. (Lubricant can, if desired, be completely omitted from the packet, or, can be included inside and outside condom 13 to contact simultaneously both surface 64 and 65.) The packet is utilized by peeling layer 41 off layer 40, by peeling the flanged surface 62 off layer 40, by manually grasping and using flange 61 to pull condom 13 over an erect penis, and by detaching flange 61 from condom 13 along line of weakening 60. In some circumstances it may be desirable to leave flange 61 attached to condom 13 while the condom is in use.

As would be appreciated by those of skill in the art, the open end 14 of a condom 13 can have many shapes other than the flange 61 shape and can still be sealingly secured to a card 43, to some layer 40 to 42, or to itself by "pursing" end 14 and adhering together the resulting contacting opposing inner surfaces of condom 13 in the manner that opposing surfaces 62 are adhered together when flange 61 is pursed as described above.

When it is desired to have a lubricant contact only surface 64 or surface 65 of condom 13, the line of weakening 60 preferably does not include perforations which pass completely through condom 13.

The resealable packet including layers 40 and 41 and resealable 48 mouth 56 can be utilized to store any desired type of condom with or without lubricant contacting either surface 64 and/or 65.

When a condom is not a conventional "cylindrical" condom, but is instead made in the process described below to be anatomically correct and to very closely conform to the shape of an erect penis, then it is important to include a reference point on the condom which correlates the top, bottom, or some other reference point on the condom with respect to a known area or point on the erect penis on which the condom is utilized. For example, in FIG. 2, indicium 67 indicates the top of the condom, i.e., indicates the portion of the condom which should be on top of, contact, and conform to the top portion of an erect penis. As used herein, the top portion of a user's erect penis is the portion closest to the user's chest. Indicium 67 or indicia can be at any desired location on condom 13, on card 43, or, if appropriate, on a layer 40 to 42. The top portion of an erect penis is indicated by reference character 69 in FIG. 5. The desired orientation of an anatomically correct condom with respect to an erect penis is obtained by rotating the condom, either before or after the condom is on the erect penis, about the longitudinal axis of the condom, which longitudinal axis generally remains parallel to the longitudinal axis of the erect penis while the condom is rotated about its own longitudinal axis. As would be appreciated by those of skill in the art, an anatomically correct condom which fits an erect penis "like a glove" basically has only one correct orientation on the erect penis and can not, as can conventional cylindrically shaped condoms, be placed on an erect penis in a variety of different orientations.

Another embodiment of the invention is illustrated in FIG. 6 and includes the step 50 of producing a computer based computer aided design (CAD) file or other file representing a three-dimensional scan of a selected erect penis. Any known prior art scanning equipment can be utilized to produce a file defining the shape and dimension of an erect penis. A series of digital photographs of the erect penis can be taken, and the resulting digital data entered into and evaluated by an appropriate computer program to produce a digital three dimensional image of the erect penis. Photographic slides or prints of pictures of an erect penis can be scanned into a computer and evaluated to produce a digital three dimensional image of the erect penis. Laser, holographic, or any other scanning equipment can be utilized to produce digital or other data defining the erect penis in three dimensions. Once a computer file is obtained which defines in three dimensions the profile of an erect penis, for example either an .stl or .slc computer file format, then in the next step 51, the computer based file is utilized by stereolithography apparatus or other apparatus to produce an actual three dimensional form or model of the erect penis. The model can be utilized as a mandrel and dipped in latex 52 in conventional fashion to produce an anatomically correct condom which closely conforms to the model. The mandrel or the digital data used to produce the mandrel can be utilized to make condoms out of materials other than latex. In the foregoing method described in this paragraph, an individual can obtain custom made condoms which closely conform to his erect penis. Such a close fit custom condom increases comfort and decreases the likelihood that the condom will slip off or leak in use. Once a computer based file is obtained which defines in three dimensions an erect penis, the file can be adjusted as desired. For example, it may be desirable to include in the condom made to fit the erect penis a small area of additional space in the area where the glans penis meets the corpus spongiosium. This small extra space would allow seminal fluid and semen to collect and would provide for less fluid built-up between the highly sensitive glans penis and the condom. Such a small area is readily compensated for by programming the computer based file to produce a model of the erect penis (or to produce a condom) which includes a small raised area which does not naturally occur and which is located in the area where the glans penis meets the corpus spongiosium. Another manner in which the computer file can be programmed is to produce a condom which has a tighter fit (i.e., a condom which is not as big or which has less resilient elastomer) near the base of the condom. Such a tighter fit could extend along one-sixteenth to two inches, preferably one-half to one inch, of the length of the condom nearer the base of an erect penis on which the condom is used to reduce the risk that seminal fluid will escape out the bottom of the condom. As would be appreciated by those of skill in the art, conventional manufacturing procedures (and not the CAD-stereolithography procedures described above) can also be utilized to make condom both with a tighter fit near the base and with the small storage area or "pocket" between the glans penis and corpus spongiosum to collect seminal fluid.

Figure 5:
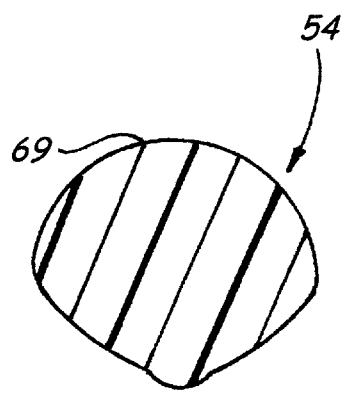
FIG. 5 is a cross-sectional view of a model of an erect penis produced in accordance with the 3D-stereolithographic method of the invention; and, FIG. 6 flow chart illustrating a method of producing an anatomically correct condom in accordance with the principles of the invention.

One advantage of utilizing the method of FIG. 6 is that the resulting three dimensional anatomical model of an erect penis has a cross section 54 similar to that shown in FIG. 5, i.e., has a cross section which is more nearly oval instead of the circular cross section suggested by conventional rolled condoms.

The method of FIG. 6 can be utilized to produce a "reference supply" consisting of a plurality of reference mandrels. Each reference mandrel has a shape and dimension different from that of the remaining mandrels in the reference supply. Each reference mandrel is dipped in latex to produce condoms which custom fit that reference mandrel. Of course, conventional methods other than dipping a mandrel in latex can be utilized to produce a condom which will custom fit a reference mandrel. The condom may or may not be fabricated from latex, as desired. If fifty or more such reference mandrels are produced to account for a range of penis shapes and sizes, then after an individual provides data defining in three dimensions (by scanning, digital photograph, etc.) his erect penis, it is not necessary to produce a mandrel replicating his erect penis. Instead, the data for his penis is compared by computer program or other means to the data defining each of the reference mandrels in the "reference supply". The reference mandrel which is closest in shape and dimension to the individual's erect penis is selected and utilized to produce condoms for the individual, or, if there is a pre-existing supply of condoms previously made utilizing the selected reference mandrel, then some of the pre-existing condoms are sent to the individual.

Having described my invention in such terms as to enable those of ordinary skill in the art to make and use the invention, and having described the presently preferred embodiments thereof, I claim:

1. An article of manufacture comprising a package including
   (a) a first layer of material;
   (b) a second layer of material sealed to said first layer;
   (c) a condom mounted on said second layer of material;
   (d) a third layer of material attached to said first layer to enclose said second layer and said condom intermediate said first and second layers; and,
   (e) lubricant sealed between one of a pair including
      (i) said first layer and said second layer, and
      (ii) said second layer and said third layer.

2. A method of producing a condom, including the steps of
   (a) producing a computer file defining in three dimensions a selected erect penis;
   (b) utilizing said computer file to produce a model of said selected erect penis; and,
   (c) utilizing said model to produce a condom.

* * * * *